United States Patent [19]

Blaricom

[11] Patent Number: 5,558,756
[45] Date of Patent: Sep. 24, 1996

[54] METHOD FOR GEO-ELECTROCHEMICAL SAMPLING

[75] Inventor: Richard Van Blaricom, Colbert, Wash.

[73] Assignee: Cominco Ltd., Vancouver, Canada

[21] Appl. No.: 460,882

[22] Filed: Jun. 5, 1995

Related U.S. Application Data

[62] Division of Ser. No. 340,890, Nov. 15, 1994.

[51] Int. Cl.⁶ .................................................. G01N 27/26
[52] U.S. Cl. ...................... 205/789.5; 204/400; 204/435; 205/632; 205/775; 205/789; 205/792.5; 205/793
[58] Field of Search ................................ 204/130, 180.1, 204/153.1, 400, 435; 205/775, 789.5, 789, 792.5, 793, 632

[56] References Cited

U.S. PATENT DOCUMENTS

| | | | |
|---|---|---|---|
| 2,614,976 | 10/1952 | Patnode et al. | 204/418 |
| 2,741,591 | 4/1956 | Dewey et al. | 204/301 |
| 2,788,319 | 4/1957 | Pearson | 204/301 |
| 2,854,393 | 9/1958 | Kollsman | 204/301 |
| 3,498,899 | 3/1970 | Kater et al. | 204/420 |
| 3,879,279 | 4/1975 | Baucke | 204/435 |
| 4,242,191 | 12/1980 | Schindler et al. | 204/420 |
| 4,913,793 | 4/1990 | Leonard | 204/433 |
| 5,071,537 | 12/1991 | Yamaguchi et al. | 204/435 |
| 5,137,608 | 8/1992 | Alar et al. | 204/130 |

FOREIGN PATENT DOCUMENTS

| | | |
|---|---|---|
| 3305962 | 8/1984 | Germany . |
| 2093193 | 8/1982 | United Kingdom . |

OTHER PUBLICATIONS

Smith et al., "Preliminary Studies of the CHIM Electrogeochemical Method at the Kokomo Mine, Russell Gulch, Colorado", J. of Geochemical Exploration, 46 (1993) p. 257–278.

Chao "Use of Partial Dissolution Techniques in Geochemical Exploration", J. of Geochemical Exploration, 23 (1984), pp. 101–135.
"New Methods of regional exploration for blind mineralization: application in the USSR", Journal of Geochemical Exploration, 43 (1992) month unavailable pp. 157–166.
"Electrogeochemical Extraction Technique in the Prospecting of Buried Gold Deposits", Journal of Geochemical Exploration, 33 (1989) month unavailable pp. 99–108.
"Relationship between Sn Mineralization and Geochemical Anomalies in Non–Residual Over–burden at Tebrong Area, Belitung, Indonesia", Journal of Geochemical Exploration, 28 (1987) month unavailable pp. 219–234.
"Electrogeochemical Techniques in Deeply Weathered Terrain in Australia", Journal of Geochemical Exploration, 21 (1984) month unavailable pp. 311–331.
"Geochemical exploration in thick transported overburden, Eastern China", Journal of Geochemical Exploration, 33 (1989) month unavailable pp. 155–169.
"Development and Testing of the CHIM Electrogeochemical Exploration Method", Seventh Annual V. E. McKelvey Forum on Mineral and Energy Resources, 1991, pp. 74.

(List continued on next page.)

*Primary Examiner*—T. Tung .
*Attorney, Agent, or Firm*—Oyen Wiggs Green & Mutala

[57] ABSTRACT

This invention relates to a novel geo-electro-chemical sampling electrode and process. More specifically, this invention pertains to a novel ion collection electrode, and process, which can be used in the remote sampling of ions contained in ground water. This invention consists of a geo-electrochemical sampling apparatus comprising a hollow electrically non-conductive casing; an opening in the casing for enabling ions to be transported from the exterior of the casing to the interior of the casing, a cathode positioned in the interior of the casing, and electrically connected to the exterior of the casing; and, ion exchange resin contained in the interior of the casing between the cathode and the opening.

10 Claims, 6 Drawing Sheets

OTHER PUBLICATIONS

"Soil Conductivities: Assessment of an Electrogeochemical Exploration Technique", Geochemical Exploration 1974 month unavailable, pp. 101–116.

"Use of Partial Dissolution Techniques in Geochemical Exploration", Journal of Geochem–ical Exploration, 23 (1984) month unavailable pp. 101–135.

"The Method of Partial Extraction of Metals in a Constant Current Electrical Field for Geochemical Exploration", Journal of Geochemical Exploration, 23 (1985) month unavailable pp. 27–33.

"Electrochemical Technique for Exploration of Base Metal Sulphides", Journal of Geo–Chemical Exploration, 25 (1986) month unavailable pp. 389–396.

"Preliminary Studies of the CHIM *Electrogeochemical* Method at the Kokomo Mine, Russell Gulch, Colorado", Journal of Geochemical Exploration, 46 n 3 Feb., 1993, pp. 257–278.

"Electrogeochemical Patterns in Surface Soils–Detection of Blind Mineralization Beneath Exotic Cover, Thalanga, Queensland, Australia", Journal of Geochemical Exploration, 28, 28 n 1–3 Jun., 1987.

"Exploration Geochemistry in Some Low–Latitude Areas–Problems and Techniques", Trans–actions of the Institution of Mining & Metallurgy, Section B, V. 96, Aug., 1987 pp. B97–B116.

Smith et al., "Preliminary Studies of the CHIM Electrogeochemical Method at the Kokomo Mine, Russell Gulch, Colorado", J. of Geochemical Exploration, 46 (1993) month unavailable, p. 257–278.

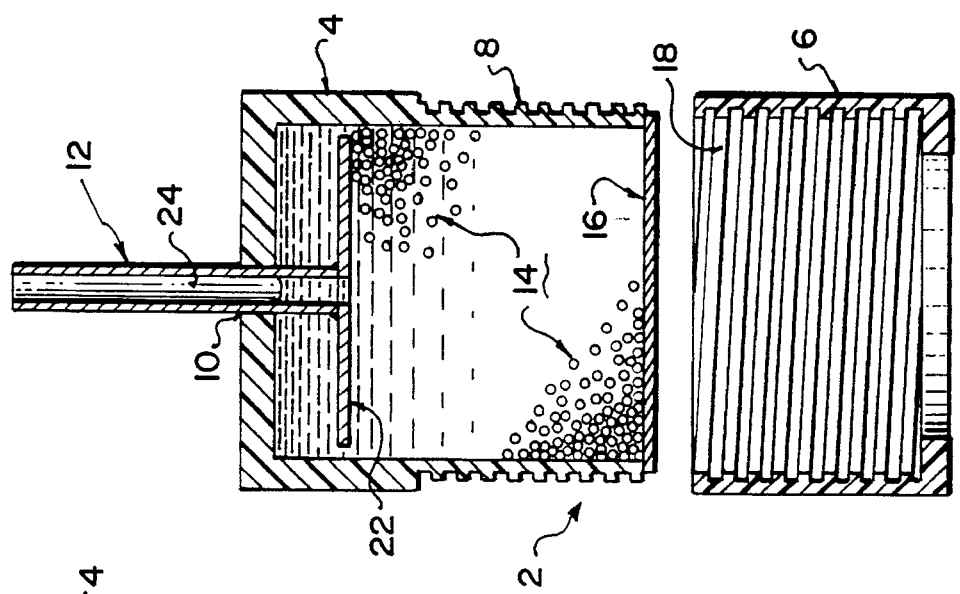
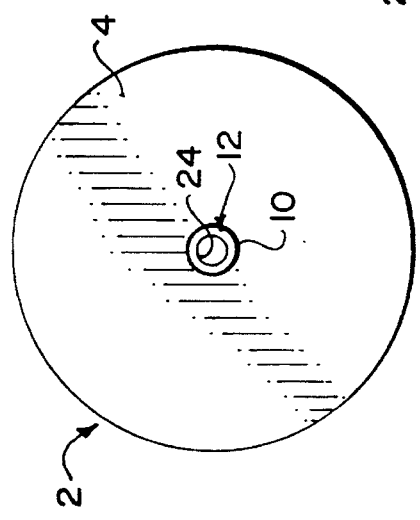
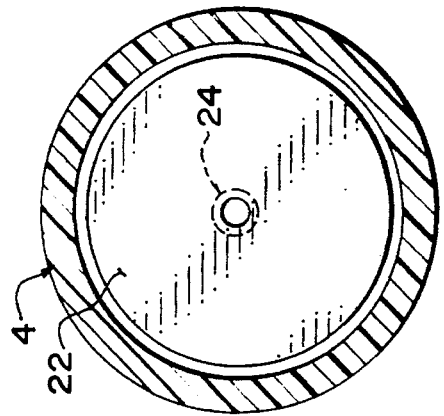
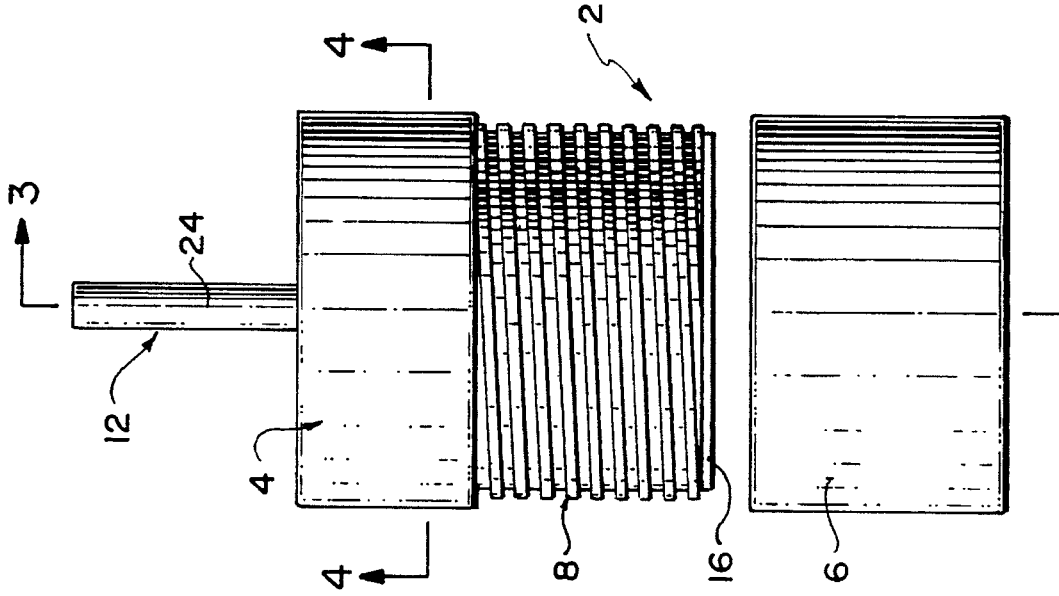
FIG. 1
FIG. 2
FIG. 3
FIG. 4

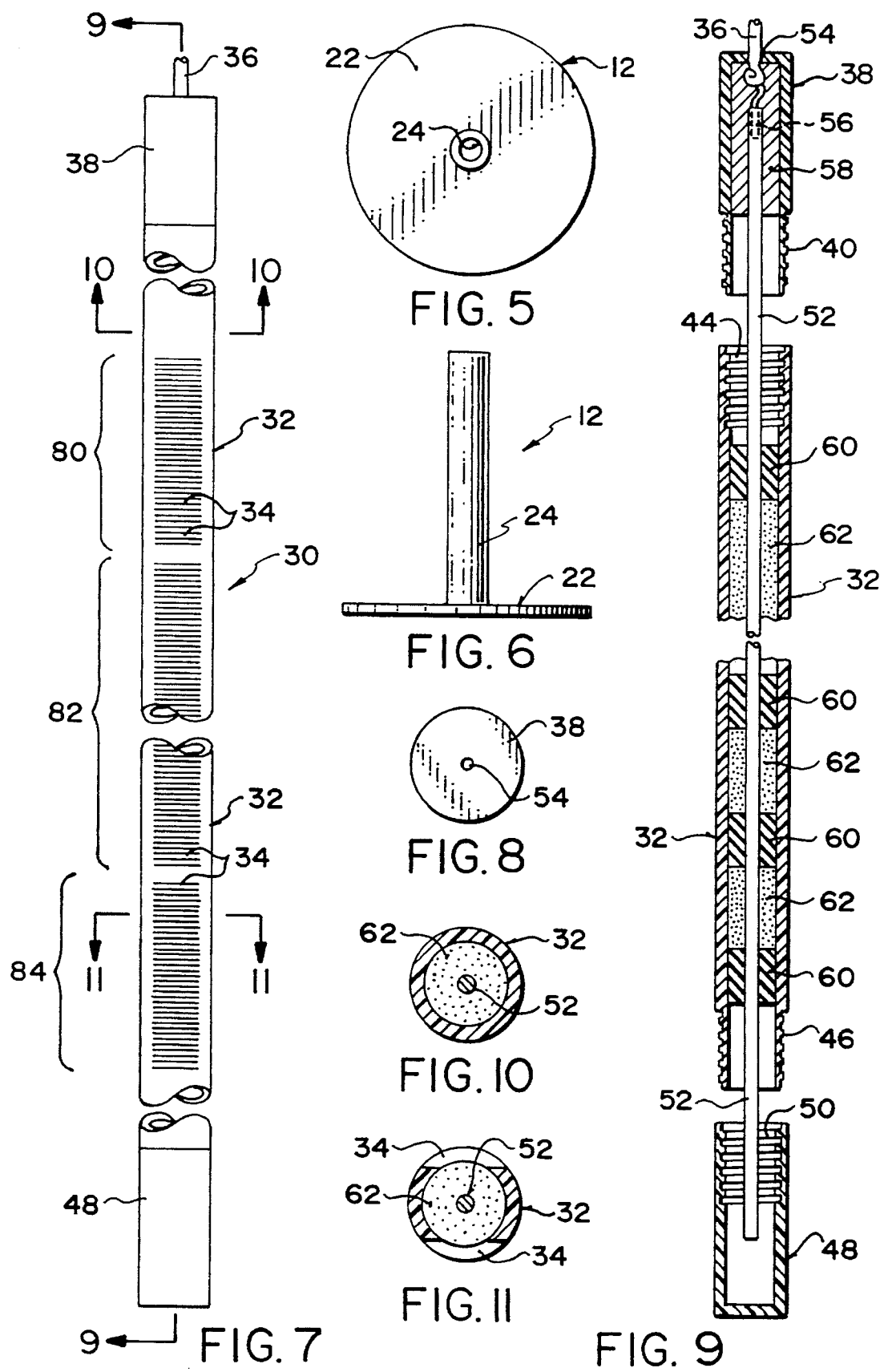

METHOD FOR GEO-ELECTROCHEMICAL SAMPLING

This is a division of application Ser. No. 08/340,890, which was filed Nov. 15, 1994.

FIELD OF THE INVENTION

This invention relates to a novel geo-electrochemical sampling electrode and process. More specifically, this invention pertains to a novel ion collection electrode, and process, which can be used in the remote sampling of ions contained in ground water, either naturally occurring or from anthropologic sources.

BACKGROUND OF THE INVENTION

The electrogeochemical exploration method, CHIM, developed over twenty years ago in the former Soviet Union, is claimed to be a means of collecting ions emanating from ore deposits concealed by thick cover (Goldberg et al., 1990). Available treatises on CHIM (the term is an acronym derived from the Russian phrase "Chastichnoe Izvlechennye Metallov", meaning partial extraction of metals) in the English language are limited. Summaries may be found in Shmakin (1985), Bloomstein (1990), and Antropova et al., (1992). The method is based on the premise that an applied electric field will drive ions in the soil into specially designed collector electrodes. Ions accumulate in an electrolyte within the electrode. The electrolyte, typically nitric acid of 2N to 4N concentration, also serves to conduct current from the power source to the soil through a low-permeability membrane of synthetic parchment located at the base of the electrode.

The CHIM technique can best be described as an geo-electrogeochemical sampling method. It uses a DC electrical current to move mobile cations into special fluid-filled cathodes placed spatially on the earth's surface. Cation-collector electrodes have been designed and developed by the United States Geological Survey (USGS) to practice the CHIM method. They are relatively easy to use and clean, hold liquid well, and have a transparent body so that field crews can monitor for leaks or other problems. The cation collectors used for tests conducted at the Kokomo Mine, Russell Gulch, Colo., have an inside diameter of 1.625 inches (4.128 cm) and an operational capacity of 150 ml.

Electrical contact to the ground is made through a disk of artificial parchment (type 1470) manufactured by the James River Paper Co., Parchment, Mich. The parchment disks are cut to fit the lower cap and are held in place by an O-ring seal. In the absence of seal leaks, the electrode will lose about 5–10 ml of electrolyte through the parchment in 24 hours. A 99.6% pure titanium rod, 5 mm in diameter and 20 cm long, is used as the inner working cathode. The electrolyte used as the cation-collecting medium is 4N reagent-grade nitric acid.

The electrical current, generally ranging from 0.1 to 0.5 A, is conducted through the electrode for time intervals of several hours to several days. At the end of this time, the electrolyte and inner electrodes are collected and analyzed for elements of interest. An important aspect of the CHIM method is that it samples only ions mobile in an electric field as opposed to the total quantity of a particular element in the soil near an electrode. Where the mobile ions are related to a geochemical halo developed in cover above a deposit, CHIM samples may provide better definition of the concealed deposit than standard geochemical methods.

David B. Smith et al., in an article entitled "Preliminary Studies of the CHIM Electrogeochemical Method at the Kokomo Mine, Russell Gulch, Colo.", Journal of Geochemical Exploration, 46 (1993), page 257–278, disclose the results of preliminary tests conducted at the Kokomo Mine, using the CHIM electrogeochemical method.

Specifically, the U.S. Geological Survey started a study of the CHIM method by conducting tests over a precious- and base-metal-bearing quartz vein covered with 3 m of colluvial soil and weathered bedrock near the Kokomo Mine, Colorado. The tests show that the CHIM method gives better definition of the vein than conventional soil geochemistry based on a total-dissolution technique. The CHIM technique gives reproducible geo-chemical anomaly patterns, but the absolute concentrations depend on local site variability as well as temporal variations. Weak partial dissolutions of soils at the Kokomo Mine by an enzyme leach, a dilute acetic acid leach, and a dilute hydrochloric acid leach show results comparable to those from the CHIM method. This supports the idea that the CHIM technique is essentially a weak in-situ partial extraction involving only ions able to move in a weak electric field.

The technique uses a DC electrical current introduced into the earth to draw mobile cations into specially designed cathodes. Ions collected in this manner constitute a geochemical sample of mobile ions extracted from soil in the vicinity of the electrode. The technique may be thought of as an in-situ partial chemical extraction.

The overall equipment used in the studies at the Kokomo Mine is generally similar to the Russian CHIM equipment in electrical capacity, with the addition of a multichannel, recording, ampere-hour meter. The USGS system has a capacity of 31 channels, 15 kW, 1000 V, and 43 A. The principal components of the system are (1) power source, (2) ampere-hour recorder, (3) current control rheostats, (4) current distribution cables, and (5) cation-collector electrodes (FIG. 2). The power source is a 15 kW diesel motor generator providing AC power to Zonge GGT-25 transmitter. DC power from the GGT=25 transmitter goes to individual anode and cathode ampere-hour sensor units where the power is split into 31 channels. Each of the 62 individual channels may be monitored for current, and the ampere-hours delivered to each channel are recorded. From the ampere-hour recorder, current goes to banks of rheostats that control current to each cation collector, and from the rheostat banks to multiconductor distribution cables. Take outs on the distribution cables then deliver current to individual electrodes. For studies at the Kokomo Mine, only cation Collectors were used. The positive current conductor was directly connected to 3 or 4 graphite bars buried in the ground, salted, and watered. These were placed about 100 m from the cathode array.

Many unsolved problems remain not only in the utilization of the CHIM method as an exploration tool, but also in the basic understanding of the electrochemical processes involved. The major issues and problems include the following:

1. Anion collection. Pathfinder elements such as Au, As, and Sb may be present as anionic species in the near-surface environment (Stumm and Morgan, 1981; Mann, 1984; Webster, 1986). Russian literature translated in Bloomstein (1990) mentions briefly the importance of collecting and analyzing anions but does not give any data or case histories.

2. Ion mobility in the vadose zone. The mechanism of ion mobility in an electric field in dilute solution is well understood. However, in the vadose zone, where most CHIM collection occurs, and in the presence of clays and organic matter that absorb ions, the process of ion mobility is not well understood. If relative mobilities in the unsaturated soil are significantly different than those observed in dilute solution, selective collection could require alteration of conventional interpretation of CHIM data.

3. Destabilization processes at the soil-electrode interface. Elements present as either positive or negative complexes present problems for the CHIM technique. Such complexes are not stable over a wide range of pH. At the electrode-soil interface, these complexes may be destabilized and thus prevented from entering the low-pH electrolyte.

4. Problematical analytical methods. The nitric acid solution from a CHIM cation collector poses analytical problems because the sample contains very low concentrations of some important pathfinder cations such as Au in a matrix containing high concentrations of major cations such as Ca, Mg, Na, Fe, etc. As part of our CHIM research, reference samples of the nitric acid solution from the CHIM runs have been prepared for interlaboratory comparisons.

5. CHIM vs. partial extractions. In the study at the Kokomo Mine, certain partial-dissolution techniques gave results at least as good as the more time-consuming and expensive CHIM method. More comparisons need to be made for various types of mineral deposits in a variety of geologic settings to determine if results from the CHIM method can be duplicated with partial-dissolution techniques.

SUMMARY OF THE INVENTION

The invention is directed to a geo-electrochemical sampling apparatus comprising: (a) a hollow electrically non-conductive casing; (b) an opening in the casing for enabling ions to be transported from the exterior of the casing to the interior of the casing; (c) an electrode positioned in the interior of the casing, the electrode being electrically connected to the exterior of the casing and being of a charge attractive to the ions; and (d) an ion exchange resin contained in the interior of the casing between the electrode and the opening.

The electrode according to the invention can be a cathode and the ions can be cations. In the apparatus, a non-ion containing water such as distilled water or purified water can be contained in the interior of the casing. The apparatus can include means for applying a negative voltage to the cathode. A semi-permeable membrane can be positioned between the opening in the casing and the ion exchange resin contained in the interior of the casing. The semi-permeable membrane can be parchment.

The cathode can be constructed of titanium or a disk of titanium. The casing can be constructed of two detachable components and can be constructed of plastic. The apparatus can include an azimuth partition which divides the ion exchange resin into two groups.

The casing can have the shape of a hollow cup, with a cap which can be detachably secured to the open end of the cup, the opening can be located in the base of the cup or cap, and the cathode can be a disk located at the base of the cup or cap and can be electrically connected to the exterior through an opening in the base of the cup or cap.

The casing can be in the form of a hollow cylinder. The casing can have an elongated cylindrical shape with walls, the cathode can be a metal tube fixed to a flat disk axially disposed in the interior of the cylindrical casing, the ion exchange resin can be held in the volume between the cylindrical casing and the flat disk, and at least one opening for ion exchange can be located in the walls of the casing.

In another aspect, the casing can have an elongated hollow cylindrical shape, the cathode can be an elongated metal rod extending through substantially the length of the casing, the ion exchange resin can be held in the annular volume between the rod and the walls of the casing, and the one or more openings can be in the circumferential wall of the casing.

The ion exchange resin can be separated into a first upper group, a second middle group and a third bottom group and the casing can have three sets of openings therein which correspond with the first, second and third groups of ion exchange resin.

The metal rod can be held in place in the casing by electrically inert stoppers to provide an annular volume between the cylindrical casing and the internally disposed elongated rod. A cap can be detachably secured to one end of the elongated cylindrical casing and a second cap can be detachably secured to an opposite end of the elongated cylindrical casing. The casing can be constructed of polyvinylchloride. The ion exchange resin can be contained in a package which can be installed or removed from the apparatus as a unit.

The apparatus can include first and second openings in the casing and an azimuth partition in the casing which divides the ion exchange resin in the casing into first and second groups so that the ions received through a first opening and exchanged with the ion exchange resin in the first group are separate from the ions received through a second opening and exchanged with the ion exchange resins in the second group.

The invention also pertains to a method of sampling and analyzing ground water for ions which comprises: (a) applying a high negative voltage to a cathode proximate to the ground water thereby attracting metallic cations in the ground water to the cathode; (b) exchanging the metallic cations for hydrogen ions in a hydrogen ion charged ion exchange resin to thereby deposit the metallic cations on the resin and release the hydrogen ions to the cathode; and (c) analyzing the cation exchanged resin for metal concentration.

The ion exchange resin which holds the deposited metallic cations can be ashed and the metallic cations can be analyzed. The ashed ion exchange resin can be analyzed by inductively coupled plasma mass spectrometry.

The invention is also directed to a method of focusing an ion collection electrode which is used to attract ions in ground water which comprises: (a) deploying a central collection electrode on or near the surface of ground in which ground water is found, and applying a high positive or negative voltage to the electrode proximate to the ground water to attract ions of opposite charge to the collection electrode; and (b) deploying at least one peripheral focusing electrode on or near the surface of the ground adjacent to but spaced from the central collection electrode and applying approximately the same voltage as that applied to the central collection electrode to thereby focus the ions attracted to the central collection electrode.

A negative voltage can be applied to the collection electrode and metallic cations in the ground water can be attracted to the collection electrode. At least four peripheral collectrodes can be spatially deployed around the periphery of the central collection electrode so that the central collection electrode tends to attract metallic cations in the ground water from beside and below the central collection electrode.

The invention is also directed to a method of focusing a downhole collection electrode to sample ions in ground water which comprises: (a) dividing an upper region of the collection electrode into a first compartment containing ion exchange resin; (b) dividing a mid-region of the collection electrode into a second middle compartment containing ion exchange resin; (c) dividing a bottom region of the collection electrode into a third bottom compartment containing ion exchange resin; (d) deploying the collection electrode in a drill hole below ground level; (e) applying a high potential to the collection electrode, whereby the first compartment of the collection electrode tends to attract ions of an opposite charge from above and beside the upper region of the collection electrode to the ion exchange resin contained in the first compartment; whereby the second compartment of the collection electrode tends to attract ions of opposite charge located laterally of the collection electrode to the ion exchange resin contained in the second middle compartment; and whereby the third bottom compartment of the collection electrode tends to attract ions of opposite charge located beside and below the lower region of the collection electrode to the ion exchange resin contained in the third bottom compartment of the collection electrode.

A negative voltage can be applied to the collection electrode and metallic cations in the ground water can be attracted to the first, second and third compartments of the collection electrode.

The invention also pertains to a method of determining metal ion contamination in ground waters in the region of an industrial installation, which comprises deploying an array of collection electrodes with ion exchange resins in the region of the industrial installation, negatively charging the collection electrodes on a periodic basis to attract metal cations in the ground water surrounding the industrial installation, to the respective collection electrodes and ion exchange resins, and sampling on a periodic basis the ion exchange resins to determine the extent of metal ion contamination in the ground water.

Involved in each sampling procedure will be a remote return electrode necessary to complete the current path. The remote return electrode is the opposite polarity (voltage) to the collecting electrode. The remote electrode should be constructed of suitable material such as stainless steel. The remote return electrode can be, as well, a collectrode filled with ion exchange resins to sample the appropriately charged ions which will be attracted.

BRIEF DESCRIPTION OF THE DRAWINGS

In drawings which illustrate specific embodiments of the invention but which should not be construed as limiting or restricting the field or scope of the invention in any way.

FIG. 1 illustrates a front elevation exploded view of a surface collectrode.

FIG. 2 illustrates a plan view of the surface collectrode.

FIG. 3 illustrates a section view taken along section line A—A of FIG. 1.

FIG. 4 illustrates a section view taken along section line B–B of FIG. 1.

FIG. 5 illustrates a plan view of the cathode of the surface collectrode.

FIG. 6 illustrates an elevation of the cathode of the surface collectrode.

FIG. 7 illustrates a plan view of a down-hole collectrode.

FIG. 8 illustrates a left elevation of the down-hole collectrode.

FIG. 9 illustrates a section view taken along section line A—A of FIG. 7.

FIG. 10 illustrates a section view taken along section line B—B of FIG. 7.

FIG. 11 illustrates a section view taken along section line C—C of FIG. 7.

DETAILED DESCRIPTION OF SPECIFIC EMBODIMENTS OF THE INVENTION

Figure 12:
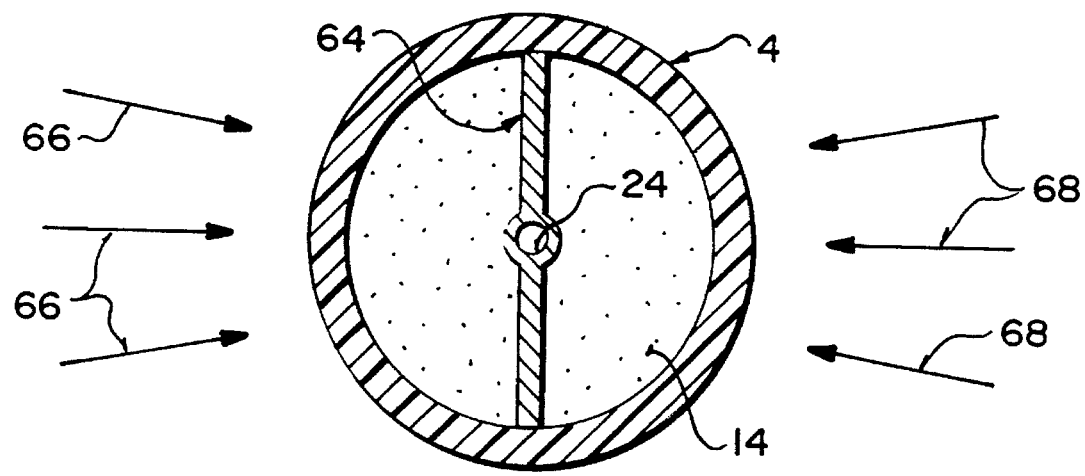
FIG. 12 illustrates a section view taken along section line B—B of FIG. 1, but including an azimuth partition.

I have invented a novel collection electrode (collectrode) and methods of using the collectrode. The apparatus and methods of this invention have the ability to focus the ionic beam (the collecting path) so that one can determine sample depth from the surface collectrodes and azimuth, and elevation angle and distance from the downhole collectrodes. The focus is built into the downhole electrode but focusing electrodes are needed to focus the surface electrodes. The compiled information allows one to more accurately determine the location from which the specific ions were collected. The ability to focus the ionic beam path is extremely useful, allowing one to be very selective. Ion exchange resins are used as the ion collectors. The collectrode can be filled with generally ion free water such as distilled water or purified water to facilitate ion transfer.

Referring to the drawings, FIG. 1 illustrates a front elevation exploded view of a surface collectrode 2, which is one embodiment of the invention. The collectrode 2 is constructed basically in the shape of a hollow cylinder, which is constructed in two parts, a hollow plastic body 4, preferably made of 80 polyvinylchloride (PVC), and a hollow screw cap 6, also constructed preferably of 80 polyvinylchloride. The PVC body 4 has right hand male square threads 8 formed along the external part of its body which intersects with the interior of the screw cap 6. The cap 4 has a cathode 12 protruding from its solid base end. Corresponding right hand female square threads are formed in the interior of the cap 6, to mate with the male threads of body 4. The female threads are not visible in FIG. 1.

FIG. 2 illustrates a plan view of the surface collectrode 2. The plastic body 4 has a circular cross-section, with a circular hole 10 formed in the top central area thereof.

FIG. 3 illustrates an exploded section view taken along section line A—A of FIG. 1. As seen in FIG. 3, the plastic body 4 has a cathode 12 extending through the hole 10 formed in the top surface of the plastic body 4. Right hand square cut male threads 8 are formed around the circumference of a lower portion of plastic body 4. The cylindrical interior cavity of the hollow plastic body 4 is filled with ion exchange resin 14, preferably Ionac (trade-mark) C-267, available from Sybron Company. Either cation exchange resins or anion exchange resins can be used depending on the potential applied (negative or positive) and the type of ions selected for collection (either cations or anions). A semi-permeable membrane 16, which is in the shape of a disk, fits along the base of the plastic body 4, and holds the ion exchange resins 14 and ion free water in place in the interior of cap 4. The semi-permeable membrane is a cut circular disc of parchment 01651 #120 manufactured by James River Paper Co.

FIG. 3 also illustrates in section view the construction of the cap 6. Right hand female square threads 18 are formed in the interior cylindrical walls of the cap 6 and mate with the right hand square male threads 8 of the plastic body 4. The number of male threads 8 and the number of female threads 18 should correspond so that the cap 6 can be screwed onto the plastic body 4 to the point where semi-permeable disk membrane 16 fits snugly at the interior base of cap 6, and abuts circular hole 20, which is formed in the bottom flat circular base of cap 6. Ion exchange into and out of the ion exchange resin beads 14 is conducted through hole 20 and semi-permeable membrane 16.

FIG. 4 illustrates a section view taken along section line B—B of FIG. 1. The plastic body 4 has a hollow circular configuration, in cross-section, and contains the ion exchange resin 14. A tube 24, which forms part of the central cathode, is located in the central axial area of the plastic body 4.

FIG. 5 illustrates a plan view of the cathode 12, which is of a circular configuration comprising cathode disk 22 and cathode tubing 24.

FIG. 6 illustrates an elevation view of the cathode 12, and specifically the cathode disk 22 and the cathode tubing 24. The disk 22 is preferably formed of titanium plate. The tube 24 is also preferably formed of titanium. The tube 24 is vertically affixed in a suitable manner such as welding to the central area of one side of the disk 22. As seen in FIGS. 1 and 3, the cathode tube 24 protrudes through the hole 10 formed in the top of the plastic body 4.

FIG. 7 illustrates a plan view of a down-hole collectrode 30, which is a second embodiment of the invention. This design of collectrode 30 is suitable for downhole sampling ground water in a hole drilled in the ground. As shown in FIG. 7, the down-hole collectrode 30 has a long, cylindrical configuration comprising a cylindrical body 32, preferably constructed of Schedule 80 polyvinylchloride pipe, which has a first cap 38 secured to one end thereof, and a second cap 48 secured to the opposite end thereof. A series of linear slots 34 are cut in parallel groups along a major interior portion of the length of the cylindrical main body 32, between end caps 38 and 48. An electrical cord 36 extends from the free end of first cap 38.

FIG. 8 illustrates a left elevation of the down-hole collectrode 30. Specifically, FIG. 8 illustrates the cap 38, which has a circular cross-section and a central hole 54 through which electrical cord 36 is passed.

FIG. 9 illustrates a section view taken along section line A—A of FIG. 7. FIG. 9 illustrates in detail the construction of the hollow cylindrical main body 32, and the manner in which the male threads on first end cap 38 fits by female threads at one end of main body 32, and the female threads of the second cap 48 fits by male threads at the other end of main body 32. These threads can be reversed, or both sets can be male or female. First cap 38 has a hollow, cylindrical configuration with a hole 54 formed in the flat base end thereof, which accommodates the electrical cord 36. At the other end, first cap 38 has right hand male square threads 40 formed at the end opposite hole 54. These right hand male threads 40 fit within corresponding right hand female threads 44 formed in the interior at first end of hollow cylindrical body 32. At the opposite end, the main body 32 has formed in the exterior end surface thereof right hand male square threads 46, which correspond to and mate with right hand female square threads 50, which are formed in the interior of second cap 48.

Extending along most of the interior axial length of the down-hole collectrode 30 is an electrically conducting rod 52, which is preferably formed of a metal such as titanium or stainless steel. The electrical cord 36, which enters the interior of first cap 38 through end hole 54, is connected to the adjacent end of the steel rod 52 by silver solder 56. First cap 38 is then preferably filled with an electrically inert potting compound to hold the cord 36 and the end of the steel rod 52 in place in the interior of the cap 38 and body 32. Four spaced rubber stoppers 60 are installed throughout the axial interior of cylindrical main body 32, which encloses the main portion of the cylindrical stainless steel rod 52. The rubber stoppers compartmentalize the downhole electrode into three compartments, an upper compartment, a middle compartment and a lower compartment. Three batches of ion exchange resin 62 are enclosed in the respective individual annular compartments formed by the interior walls of the cylindrical main body 32, the exterior surface of the long steel rod 52, and the stoppers 60. The electrical cord 36 is preferably flexible twelve gauge strand copper insulated with a suitable electrical insulation. The main cylindrical body 32, the first cap 38 and the second cap 48 are preferably formed of 80 Polyvinylchloride pipe. The ion exchange resin is preferably Ionac™ C-267 and is available from Sybron Company. As discussed in detail later, the central portion of the downhole collectrode may also contain one or more azimuth partitions (not shown). These partitions facilitate determining the direction (azimuth) that the ions originate from.

As can be seen in plan view in FIG. 7, the series of parallel linear slots 34 are arranged in three groups. These three groups correspond respectively with the locations of the three compartments in the interior of the cylindrical body 32 between the four stoppers 60 which hold the ion exchange resin 62 in three groups. This open slot pattern allows direct communication between the interior and exterior and permits the external ions to pass through the slots into the ion exchange resins.

FIG. 10 illustrates a section view taken along section line B—B of FIG. 7. In particular, FIG. 10 illustrates the circular cross-sectional configuration of main cylindrical body 32, and centrally disposed rod 52. The ion exchange resin 62 is confined in the interior annular volume formed between outer cylindrical body 32 and internal rod 52.

FIG. 11 illustrates a section view taken along section line C—C of FIG. 7. As with FIG. 10, the ion exchange resin 62 is held in place in the annular volume formed between outer cylindrical body 32 and central rod 52. FIG. 11 is helpful for illustrating the manner in which the slots 34 are formed in opposite walls of cylindrical body 32.

FIG. 12 illustrates a section view of a surface electrode taken along section line B—B of FIG. 1, but including an azimuth partition. Specifically, the collectrode illustrated in FIG. 12 is of the same general construction as the collectrode illustrated in FIG. 4 and discussed previously. It has a hollow plastic body with a hollow circular configuration in cross-section and contains an ion exchange resin 14 and a central tube 24. However, the configuration illustrated in FIG. 12 includes an azimuthal partition plate 64, which isolates the ion exchange resin 14 into two compartments, one on each side of the collectrode. As indicated by the arrows 66 on the left side, and the arrows 68 on the right side, which represent ion travel paths, the ions on each side of the collectrode are attracted to the proximate ion exchange resins on respective sides of the partition 64. In this way, by analyzing the resin on the respective side of the partition 64, it is possible to determine which side of the collectrode the ions were attracted from. While FIG. 12 illustrates a surface collectrode, it will be understood that the azimuthal partition 64 can, for instance, be installed in the middle ion exchange resin compartment of the collectrode illustrated in FIG. 9. The concepts of upper, middle and lower ion exchange resin compartments in the downhole collectrode are discussed below in connection with FIG. 17.

Adapting the configuration illustrated in FIG. 12 to a downhole collectrode, considering only the middle compartment of the downhole collectrode, and an azimuthal partition in the middle compartment, only those ions flowing from the left, represented by arrows 66, will be collected by the ion exchange resin in the left hand portion of the collectrode, while only those ions flowing from the right, represented by arrows 68, will be collected by the ion exchange resin on the right side of the collectrode. This procedure will allow the collectrode user to determine which side (azimuth) has the greater concentration of the ions of interest.

Figure 13:
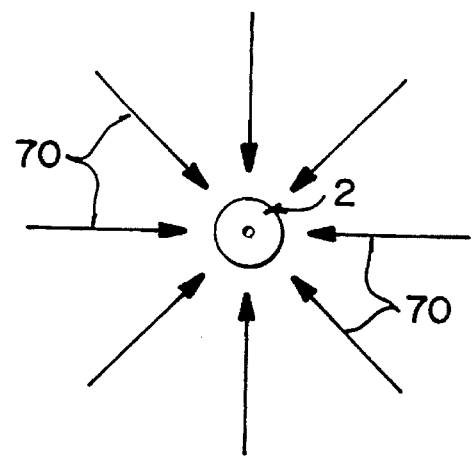
FIG. 13 illustrates a plan view of a surface collectrode and the manner in which ions in the earth are circumferentially attracted to the collectrode.

FIG. 13 illustrates a plan view of a surface collectrode and the manner in which ions in the earth are circumferentially attracted to the collectrode. Without the use of focusing electrodes, the ions represented by arrows 70 are attracted to the surface collectrode 2 according to a 360° pattern, as illustrated in FIG. 13.

Figure 14:
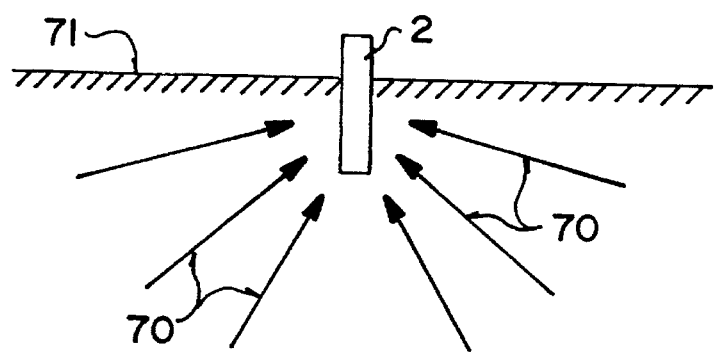
FIG. 14 illustrates an elevation view of the surface collectrode placed in the earth, and the manner in which ions in the earth are hemispherically attracted to the collectrode.

FIG. 14 illustrates an elevation view of the surface collectrode placed in the earth, and the manner in which ions in the earth are hemispherically attracted to the collectrode. As seen in FIG. 14, the collectrode 2 is partially immersed in the surface of the earth 71. As can be seen, the ions, represented by arrow 70, are attracted from all sides and below the collectrode 2, according to a hemispherical pattern.

Figure 15:
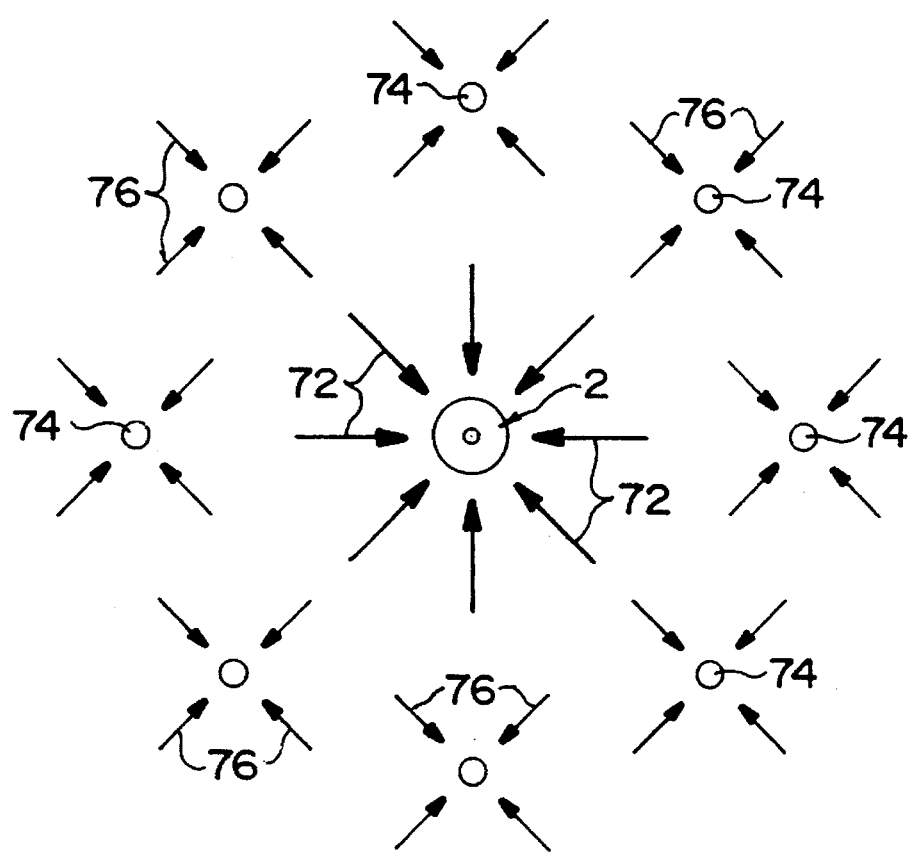
FIG. 15 illustrates a plan view of a surface collectrode and an array of ancillary focusing electrodes deployed around the periphery of the collectrode, and the manner in which ions in the earth are attracted to the collectrode and the dispersed focusing electrodes.

FIG. 15 illustrates a plan view of a surface collectrode and an array of ancillary focusing electrodes deployed around the periphery of the central collectrode, and the manner in which ions in the earth are attracted to the collectrode and the deployed focusing electrodes. As seen in FIG. 15, the surface collectrode 2 is centrally disposed, and attracts ions represented by arrows 72 from all sides. A number of focusing electrodes 74 are deployed around the periphery of the collectrode 2. These focusing electrodes 74 individually attract ions as represented by arrows 76. In this way, the ions attracted to the central collectrode 2, represented by arrows 72, are more focused and localized. The focusing collectrodes 74 generally have the same potential as the central collectrode 2.

Figure 16:
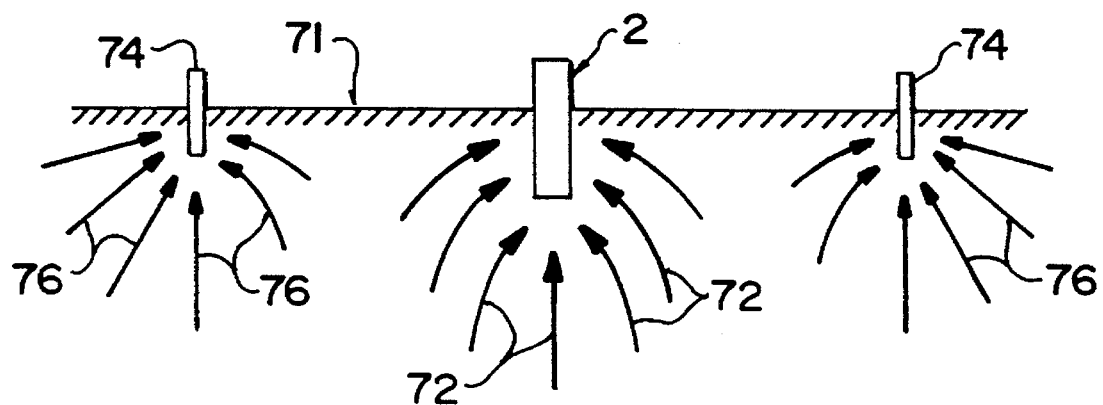
FIG. 16 illustrates an elevation view of a surface collectrode and a pair of ancillary focusing electrodes deployed on each side of the central surface collectrode, and the manner in which ions in the earth are attracted to the collectrode and the respective focusing electrodes.

FIG. 16 illustrates an elevation view of a surface collectrode and a pair of focusing electrodes deployed on each side of the collectrode, and the manner in which ions in the earth are attracted to the collectrode and the respective focusing electrodes. FIG. 16 clearly shows how the ions attracted to the central collectrode 2 are more focused or localized from below the collectrode 2, as represented by upward arrows 72. This configuration, in effect, enables the user of the central collectrode 2 to focus on ions which are in the ground water in the earth below the location of the central collectrode 2. The ion travel paths that are represented by arrows 76 below the focusing electrodes 74, are attracted to the respective focusing electrodes 74 and thus are not inclined to be attracted to the central collectrode 2. The electrode distribution pattern illustrated in FIGS. 15 and 16 can, of course, be varied to suit the individual focusing needs required to deal with the situation at hand. It will be understood that all sorts of different patterns can be used, while practicing the fundamental focusing concepts of the invention.

Figure 17:
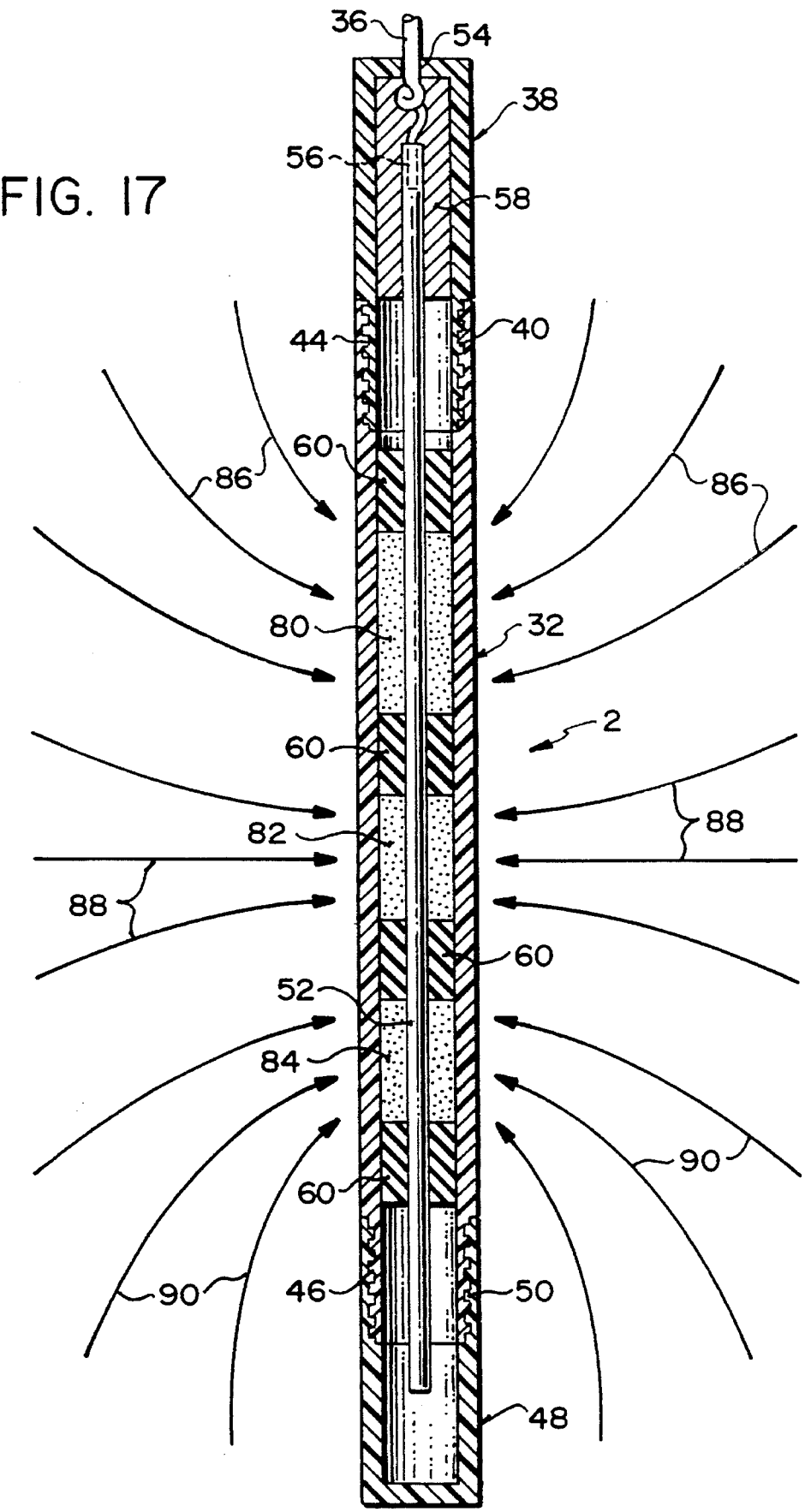
FIG. 17 illustrates an elevation section view of a downhole collectrode, and the manner in which ions in the earth are attracted to the upper, middle and lower compartments of the collectrode.

FIG. 17 illustrates an elevation section view of the downhole collectrode, and the manner in which ions in the earth are attracted to the upper, middle and lower compartments of the collectrode. As seen in FIG. 17, the fundamental design of the collectrode 2 is the same as illustrated and discussed previously in association with FIG. 9. As seen in FIG. 17, the ion exchange resins are separated into three separate compartments, namely, an upper ion exchange resin compartment 80, a middle ion exchange resin compartment 82, and a bottom ion exchange resin compartment 84. This construction enables each compartment of the downhole collectrode 2 to be focused, as indicated by the various ionic arrow patterns illustrated in FIG. 17. When the downhole collectrode is installed down a drill hole, the ions in the fluids in the downhole and the surrounding earth, located to the side and above the collectrode 2, are attracted, as represented by ion arrows 86, to the upper ion exchange resin compartment 80. In similar fashion, but in inverted pattern, the ions in the drill hole fluids and the surrounding earth below and to the lower sides of the collectrode 2, as represented by ion arrow patterns 90, are attracted to the bottom ion exchange resin compartment 84.

Meanwhile, and of particular importance, those ions which are in the drill hole fluids and the surrounding earth adjacent the middle ion exchange compartment 82 are attracted to the ion exchange resins in the middle ion exchange resin compartment 82, as represented by ion arrows 88. In this way, the middle compartment of the downhole collectrode 2 can be focused laterally, since the middle ion exchange resin compartment 82 attracts only those ions which are moving laterally from the fluids, soil and rocks to the collectrode, and specifically, the middle ion exchange resin compartment 82. Thus, by analyzing the ion exchange resins in the middle compartment 82, the collectrode user is able to determine the concentration of the ions that are distributed laterally from the downhole collectrode 2.

This is an important aspect of the invention. By segmenting the downhole electrode into three vertical sections, namely, an upper top compartment 80, a middle compartment 82, and a bottom compartment 84, the downhole collectrode can be designed to sample ions from three directions, those from above, those which move laterally from all sides of the downhole collectrode towards the middle ion exchange resin compartment 82, and those from below the collectrode. In other words, the upper compartment 80 will collect only those ions flowing down the fluids in the drill hole, and from above the collectrode 2. Similarly, the bottom ion exchange resin compartment 84 will sample only those ions flowing up the drill hole in the fluids from below the collectrode. The middle compartment 82 samples lateral ions.

If an azimuthal partition 64 is used, for instance, in the middle ion exchange resin compartment 82, then it is possible for the downhole collectrode to not only sample the ions flowing from lateral locations towards the middle compartment of the collectrode, but it is also possible to determine from which side of the collectrode the respective ions have originated. Thus it is possible to determine which side of the collectrode has the higher ion concentration. Partitions can also be installed in one or both of the upper and bottom compartments.

Figure 18:
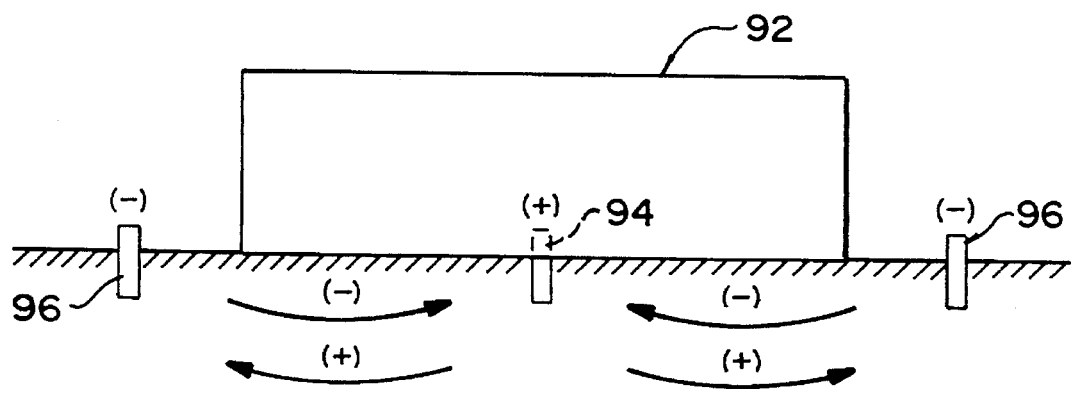
FIG. 18 illustrates an elevation view of an industrial complex with surface collectrodes distributed around the industrial complex, and the manner in which ions in the earth are attracted to the collectrodes to thereby detect ionic contamination in the earth surrounding the industrial complex.
Figure 19:
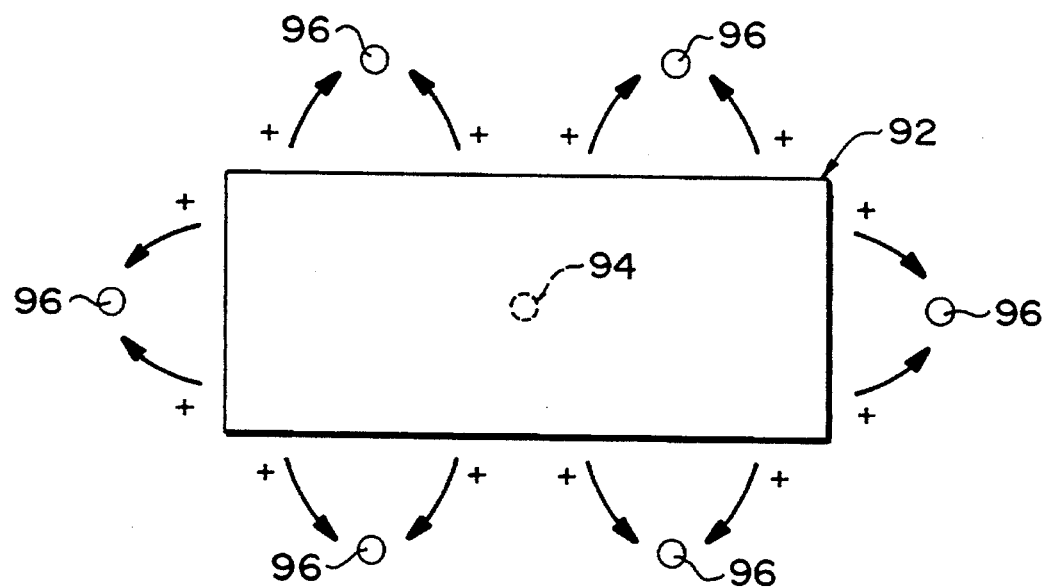
FIG. 19 illustrates a plan view of an industrial complex with collectrodes deployed around the periphery of the industrial complex.

FIG. 18 illustrates an elevation view of an industrial complex with collectrodes distributed around the industrial complex, and the manner in which ions in the earth are attracted to the collectrodes to thereby detect ionic contamination in the earth surrounding the industrial complex. FIG. 19 illustrates a plan view of the industrial complex with collectrodes deployed around the periphery of the industrial complex.

As seen in FIG. 18, several shallow drill holes are located around an industrial complex 92, and positive collectrodes 94 and negative collectrodes 96 are deployed in the respective drill holes. If need be, one or more collectrodes can be deployed in the interior of the industrial complex 92. These collectrodes can then be used to sample ions in the fluids in the earth surrounding the industrial complex 92, as represented by the directional arrows depicted in FIG. 18. FIG. 19 illustrates the same industrial complex 92, with collectrodes 96 positioned around the periphery of the industrial complex.

As a protocol, the collectrodes 94 and 96 can be energized over an extended period and the ion exchange resins which collect the ions in the earth surrounding the industrial complex 92 can be sampled on a monthly basis. Any ionic contamination in the earth and earth fluids will be attracted and collected by the respective collectrodes 94 and 96 dispersed around and throughout the industrial complex 92. By analyzing the ions collected in the ion exchange resins every month and plotting appropriate graphs, any contamination occurring in the earth either below or surrounding the industrial complex 92 can be tracked and, if necessary, curtailed by appropriate steps. The cost of operating such a collectrode pattern in an industrial complex would be minimal and since early contamination of the earth in and around the complex 92 could be quickly detected on a monthly basis, expensive cleanups and problems with the regulatory authorities can be avoided.

The collectrode of the invention can also be used from an environmental standpoint to detect leakage in various environments. The situation illustrated in FIGS. 18 and 19 represents only one application. For instance, the collectrode(s) according to the invention can be used to sample ground waters for environmental purposes such as ground water contamination from tailings and residue ponds, mines, industrial operations, dumps, stockpiles, and the like.

Application of Collectrode

The basic invention is a sampling electrode called a "Collectrode", and a method of using it. The device is intended for use in geo-electrochemical sampling. The invention incorporates and is based on several geophysical, geo-electrochemical, and electrochemical principles.

The Russians, who have experimented with the same technique (CHIM), use concentrated nitric acid in their collecting electrodes. These electrodes are unattractive and undesirable because they leak acid, which dissolves minerals in and around the collecting site. Their system represents an intrusive sampling device since it involves modifying the soil around the sampled area. The use of acids is also dangerous and can involve environment risks.

The collectrode of the invention, on the other hand, is safe from all perspectives since it contains only distilled water and benign ion exchange resins, and is to be used in the remote sampling of ions contained in ground water. The purpose of sampling of ions in the ground is that they can be extremely useful in the location of mineral deposits, ground water pollution, or the levels of ions in ground water. The technique and collectrode of the invention can sample ions from mineral deposits which have been covered by transported materials such as glacial till. The importance of being able to sample in areas covered by transported soils is that normal soil geochemical exploration is ineffective in these situations. The ions can either be free ions contained in the ground water or ions loosely attached to clays above or within the ground water table. The source of the ions can be from natural sources such as those found around mineral deposits or they can be from contamination sources.

A high negative voltage (200 to 2,000 VDC) is applied to the collectrode and the positive charged ions (cations) in the soil and water are then attracted to the negatively charged collectrode. The collectrode preferably has a titanium plate which acts as the cathode. The collectrode is filled with ion exchange resins which are hydrogen charged, and distilled water. The surface collectrode has a semipermeable membrane on the bottom of the collectrode which is placed directly in the earth. Each positively charged ion in the soil passes into the collectrode where it is exchanged with a hydrogen ion attached to the ion exchange resin beads. The released hydrogen ion then continues on to the titanium cathode. The ion exchange resins have a higher affinity for the metallic cations than they do for the hydrogen, thus all of the metallic cations drawn into the collectrode are collected on the ion exchange resins. The collectrode is filled with distilled water to facilitate transport of ions.

After the sampling is completed, a process which can take hours or days, the resins are then ashed and the ash analyzed using standard analytical techniques. The ion exchange resins and distilled water are very safe. The whole process represents a nonintrusive collecting device and sampling process. This sampling procedure can be used to sample ions from deep sources covered by over 200 feet of material. In such circumstances, conventional soil sampling procedures are generally ineffective. The ionic makeup of the soil water reflects the makeup of the solid materials in the rock/soil. The sulphide mineralization often goes into solution and creates a large ionic halo around the sulphides. The interpreted results from the subject geo-electrochemical sampling using the collectrode has identified sulphide mineral deposits which otherwise would go undetected with conventional sampling methods. This procedure is also useful in testing the ionic halo associated with some contamination spills.

The collectrode which I have invented is considerably more sensitive than the aforementioned Russian method (CHIM), or the device and method developed by the aforementioned United States Geological Survey. A significant advantage of the collectrode is that the electrical current from the collectrode can be focused, which is not done in any other procedure. The focusing of the current is accomplished by locating 4 to 8 focusing electrodes (stainless steel) around the collectrode at equal intervals. The focusing electrodes are usually placed from 3 meters to 5 meters from the collectrode. The sensitivity and the ability of the collectrode to focus the ion collection makes the method and collectrode unique over prior devices and techniques. The downhole electrodes focus the collecting currents by way of the three compartments, upper, middle, and lower, in conjunction with an azimuth portion.

The most appropriate use of the collectrode is geo-electrochemical sampling in mineral exploration, and geo-electrochemical sampling of environmental ionic contaminations. In either case, the uses are the same, locating and identifying extremely low ion levels contained within the ground water, and associated clays in soil and rocks.

The normal ion variance is largely dependent upon the hydrological gradient. Typically, there should be a large dispersion of ions down the hydrological gradient from a large deposit. There should also be dispersion of ions along fractures which commonly conduct ground water much faster than unfractured rocks. Beyond this, the ionic variances from closely spaced sample locations should not be great since the ionic dispersion is a smooth function, and the collectrode can effectively sample a large volume. This volume will be larger for higher voltages, and longer durations. The effective sampling volume can vary from one to two cubic meters up to several hundred cubic meters. The larger the volume sampled, the smaller the variance in samples. Thus the variance expected is a function of time, and current levels or amp hours. It is not possible to sample the same location twice and get the same readings since the first sample would effectively sample that volume close to the collectrode, and the second sample would effectively start sampling where the first left off.

Some ancillary material is carried into the collectrode on the ions and is not ionic. Some of this material can be organic. If it is necessary to analyze the material, special handling procedures must be used. The sampling of ions is what the collectrode has been designed for and the only limitation is that one charge of ion exchange resins is good for about 1 gram equivalent weights of ions, that is, approximately 50 grams of various cations.

The principal advantages of the collectrode of the invention are:

(1) The collectrode uses ion exchange resins and distilled water rather than dangerous acids or other caustic chemicals.

(2) The ion exchange resins used in the collectrode capture all metallic ions and are more sensitive than acids.

(3) The ion exchange resins are safe to handle, while acid electrodes require special precautions.

(4) The use of focusing electrodes has the ability to focus the current, and thus select the area to be sampled. This focusing feature concentrates current downwards for the surface collectrode, vertically and azimuthally for the down-hole collectrode. The sampling devices used in the past are non focusing electrodes. The surface electrodes used by others sample a hemisphere. The down-hole electrodes used by others sample an entire sphere around the collecting electrode. The collectrode of the invention is designed to employ the migration of ions (movement under the force of a voltage potential) rather than by diffusion. The apparatus and method of the invention rely strongly on the non-linear effects of the high voltage upon the ions.

(5) The collectrode is non-intrusive and stable over a long duration of sampling. Since the collectrode is a non-intrusive electrode, it does not react with the soil in which it is placed. The Russian system (CHIM) and possibly the U.S. Geological Survey system are intrusive systems employing nitric acid or other caustic chemicals to collect the ions.

(6) The metal cathode in the collectrode is composed of a flat titanium disk and a hollow titanium tube. This maximizes the surface area of the cathode which in turn maximizes the current flow. This design also distributes the collected ions throughout the ion exchange resin in the collectrode. The collectrode and its method of use utilizes only high voltage over long times. This maximizes the distance from which the ions can be collected.

(7) The semipermeable membrane in the surface collectrode is held firmly between two plastic lips of the outer plastic shell which are screwed together. This forms a watertight seal and maximizes accuracy.

(8) The collectrode is constructed of plastic with a titanium disk, a titanium tube, and a parchment semipermeable membrane. All of the materials used are non-toxic and no special handling procedures are needed. The ion exchange resins are contained in a paper packet or nylon netting which facilitates handling.

(9) After sampling has been completed, the ion exchange resins are ashed and then analyzed using inductively coupled plasma mass spectrometry (ICP). This is a different technique than using resins and then extracting (back stripping) the ions using acids etc. The system of the invention uses prepackaged cation exchange resins, which are placed as a packet into the holder. Voltage is then applied. At the end of a specific sampling time, the packet is removed and the resins in the packet are ashed at a high temperature such as 550 degrees F. The ash is then analyzed using (ICP). The holder is filled with distilled water during the collecting time. The process of using distilled water and cation exchange resins in a packet then ashing and analyzing is unique and a significant improvement over the Russian acid based CHIM system.

(10) The apparatus and method of the invention have a definite use both in base metal exploration and in the monitoring of low level ionic contamination dispersions from contaminated sites.

The collectrodes can also function as anion collectors by exchanging anion exchange resins for the cation exchange resins and using a high positive (+) potential rather than a high negative (−) potential. This is to be used when the ions being sampled are negatively charged ions.

The collectrode has been tested in various situations, some in the laboratory and some in the field.

EXAMPLE 1

A group of the down-hole electrodes has been used experimentally at the Magmont mine in Missouri, U.S.A., to identify mineralization in close proximity to a drill hole that had not intersected mineralization. The drilling itself did not indicate substantial mineralization in the hole. However, geo-electrochemical down-hole sampling using the collectrode indicated substantial anomalies.

The system collected about 85% of the ions expected. This is in comparison to prior art acid systems which collect about 5% to 15%. The test was useful in determining the location of subeconomic and economic grade mineral occurrences.

The area surveyed was thought to contain lead-zinc mineralization. Previously, a Geophysical Electromagnetic (EM) survey had traced the mineralization from the working face of the mine to the south for some 2500 feet. The mineralization is located in one bed which is nearly flat. However, the mineralization is narrow, on the order of 30 to 40 feet in width. The elevation of the terrain in the area is around 1300 feet and the expected elevation of the mineralization was approximately 300 feet, some 1000 feet below the surface.

Three drill holes were placed 100 feet apart MW-270, MW-271 and MW-272, to intersect the mineralization picked up in the EM survey. The drill holes were blank. This is not surprising since the EM could not accurately locate a narrow layer of mineralization some 1000 feet below the surface.

The Magmont Mining Company was stymied since it had evidence there was mineralization from the EM survey but could not intersect it with drilling. The company decided to run a downhole Geo-Electrochemical survey using the collectrode of the invention. The three holes were surveyed.

The three downhole collectrodes were placed in the holes at the expected elevation of the known mineralization. The collectrodes were energized for a period of three days, and at the end of that duration, were recovered, and the resin was removed, ashed and analyzed.

The values are reported in PPM, ug, and ug/ah; the latter, ug/ah, are probably the more useful values. In each case, drill hole MW-271 was anomalous in zinc, lead and copper. This indicates that the mineralization is close to MW-271.

Since MW-270 values were low, it was interpreted that the mineralization was immediately to the east of MW-271 and not between MW-270 and MW-271. MW-271 was also anomalous in several trace elements, such as molybdenum, cobalt and barium, all of which are trace elements for the mineralization. However, such trace elements are not as important as lead, zinc and copper.

MW-272 was also moderately anomalous in lead, zinc and copper, indicating that there may be a smaller, less significant mineralized zone nearby.

Three further holes, MW-275, MW-276 and MW-277 were also surveyed as the opportunity presented itself. MW-275 had trace mineralization present in the hole. However, the two other holes were blank, even though they were close to known mineralized holes. The challenge was to determine if anything significant was missed. MW-275 definitely had the best lead and zinc values, which is not surprising because it was in trace mineralization. The surprising feature was that the copper in MW-276 was extremely anomalous. This is probably due to some high grade copper mineralization between drill holes MW-276 and USA-5.

MW-277 had low values for lead, zinc and copper even though it was close to an ore grade intersection of MW-155. This was interpreted to indicate a rather abrupt termination of mineralization from MW-155 towards MW-277.

The level of the ions as tabulated in the following Table 1, especially as reported in ug/ah, is exceptionally high. This is probably due to two reasons. The area is mineralized, and the down-hole collectrode is an extremely efficient sampling instrument.

TABLE 1

| | VALUES REPORTED IN PPM | | | | | |
|---|---|---|---|---|---|---|
| SVL # | 28807 | 28808 | 28810 | 28812 | 28809 | 28811 |
| CLIENT # | 270 | 271 | 272 | 275 | 276 | 277 |
| ALUMINUM | 282 | 120 | 64.9 | 537 | 50 | 237 |
| ANTIMONY | <20 | <20 | <20 | <20 | <20 | <20 |
| ARSENIC | <20 | <20 | <20 | <20 | <20 | <20 |
| BARIUM | 24.7 | 128 | 122 | 155 | 85.9 | 93.7 |
| BERYLLIUM | <5 | <5 | <5 | <5 | <5 | <5 |
| BORON | 42.4 | 9.57 | 3.32 | 36.8 | 8.06 | 15.0 |
| CADMIUM | <2 | <2 | <2 | <2 | <2 | <2 |
| CALCIUM | 51100 | 171000 | 186000 | 174000 | 159000 | 147000 |
| CHROMIUM | 28.0 | 9.77 | 19.9 | 45.2 | 14.6 | 28.1 |
| COBALT | 8.98 | 5.000 | 14.1 | 6.46 | 5.000 | 5.000 |
| COPPER | 15.9 | 89.3 | 326 | 115 | 1050 | 176 |
| IRON | 4040 | 2460 | 22900 | 8270 | 1510 | 2340 |
| LEAD | 61.6 | 43.8 | 39.5 | 662 | 116 | 39.7 |
| MAGNESIUM | 28500 | 59000 | 37300 | 28600 | 77800 | 71100 |
| MANGANESE | 61.2 | 21.2 | 590 | 118 | 12.8 | 74.0 |
| MOLYBDENUM | 5 | 5 | 5 | 8.61 | 5 | 5 |
| NICKEL | 25.9 | 10 | 76.2 | 108 | 13.4 | 28.9 |
| PHOSPHORUS | 50 | 50 | 50 | 68.9 | 50 | 50 |
| POTASSIUM | 1078 | 2270 | 4610 | 25900 | 2534 | 5150 |
| SELENIUM | 50 | 50 | 50 | 50 | 50 | 50 |
| SILICON | 248 | 176 | 91.9 | 388 | 142 | 436 |
| SILVER | <5 | <5 | <5 | <5 | <5 | <5 |
| STRONTIUM | 320 | 44.0 | 238 | 1010 | 140 | 231 |
| SODIUM | 46800 | 8720 | 5930 | 38100 | 7300 | 6350 |
| THALLIUM | <10 | <10 | <10 | <10 | <10 | <10 |
| VANADIUM | <5 | <5 | <5 | <5 | <5 | <5 |
| ZINC | 28.8 | 765 | 169 | 314 | 92.4 | 77.0 |
| | VALUES REPORTED IN ug | | | | | |
| | 270 | 271 | 272 | 275 | 276 | 277 |
| grams | 48.9 | 133.8 | 75.7 | 65.8 | 44.1 | 6.4 |
| ALUMINUM | 13789.8 | 16056 | 4912.93 | 35334.6 | 2205 | 1516.8 |

TABLE 1-continued

| | | | | | | |
|---|---|---|---|---|---|---|
| ANTIMONY | 978 | 2676 | 1514 | 1316 | 882 | 128 |
| ARSENIC | <978 | <2676 | <1514 | <1316 | <882 | <128 |
| BARIUM | 1207.83 | 17126.4 | 9235.4 | 10199 | 3788.19 | 599.68 |
| BERYLLIUM | <244.5 | <669 | <378.5 | <329 | <220.5 | <32 |
| BORON | 2073.36 | 1280.47 | 251.324 | 2421.44 | 355.446 | 96 |
| CADMIUM | <97.8 | <267.6 | <151.4 | <131.6 | <88.2 | <12.8 |
| CALCIUM | 2498790 | 2.3E+07 | 1.4E+07 | 1.1E+07 | 7011900 | 940800 |
| CHROMIUM | 1369.2 | 1307.23 | 1506.43 | 2974.16 | 643.86 | 179.84 |
| COBALT | 439.122 | 669 | 1067.37 | 425.068 | 220.5 | 32 |
| COPPER | 777.51 | 11948.3 | 24678.2 | 7567 | 46305 | 1126.4 |
| IRON | 197556 | 329148 | 1733530 | 544166 | 66591 | 14976 |
| LEAD | 3012.24 | 5860.44 | 2990.15 | 43559.6 | 5115.6 | 254.08 |
| MAGNESIUM | 1393650 | 7894200 | 2823610 | 1881880 | 3430980 | 455040 |
| MANGANESE | 2992.68 | 2836.56 | 44663 | 7764.4 | 564.48 | 473.6 |
| MOLYBDENUM | 244.5 | 669 | 378.5 | 566.538 | 220.5 | 32 |
| NICKEL | 1266.51 | 1338 | 5768.34 | 7106.4 | 590.94 | 184.96 |
| PHOSPHORUS | 2445 | 6690 | 3785 | 4533.62 | 2205 | 320 |
| POTASSIUM | 52714.2 | 303726 | 348977 | 1704220 | 111749 | 32960 |
| SELENIUM | 2445 | 6690 | 3785 | 3290 | 2205 | 320 |
| SILICON | 12127.2 | 23548.8 | 6956.83 | 25530.4 | 6262.2 | 2790.4 |
| SILVER | <244.5 | <669 | <378.5 | <329 | <220.5 | <32 |
| STRONTIUM | 15648 | 5887.2 | 18016.6 | 66458 | 6174 | 1478.4 |
| SODIUM | 2288520 | 1166736 | 448901 | 2506980 | 321930 | 40640 |
| THALLIUM | <489 | <1338 | <757 | <658 | <441 | <64 |
| VANADIUM | <244.5 | <669 | <378.5 | <329 | <220.5 | <32 |
| ZINC | 1408.32 | 102357 | 12793.3 | 20661.2 | 4074.84 | 492.8 |

| ALL VALUES REPORTED IN ug/ah | | | | | | |
|---|---|---|---|---|---|---|
| DRILL HOLE | 270 | 271 | 272 | 275 | 276 | 277 |
| ah | 17.28 | 9.15 | 24.34 | 49 | 10.865 | 15.612 |
| ALUMINUM | 798 | 1755 | 202 | 721 | 203 | 97 |
| ANTIMONY | <57 | <292 | <62 | <27 | <81 | <8 |
| ARSENIC | 57 | 292 | 62 | 27 | 81 | 8 |
| BARIUM | 70 | 1872 | 379 | 208 | 349 | 38 |
| BERYLLIUM | <14 | <73 | <16 | <7 | <20 | <2 |
| BORON | 120 | 140 | 10 | 49 | 33 | 6 |
| CADMIUM | <6 | <29 | <6 | <3 | <8 | <1 |
| CALCIUM | 144606 | 2500525 | 578480 | 233657 | 645366 | 60261 |
| CHROMIUM | 79 | 143 | 62 | 61 | 59 | 12 |
| COBALT | 25 | 73 | 44 | 9 | 20 | 2 |
| COPPER | 45 | 1306 | 1014 | 154 | 4262 | 72 |
| IRON | 11433 | 35972 | 71221 | 11105 | 6129 | 959 |
| LEAD | 174 | 640 | 123 | 889 | 471 | 16 |
| MAGNESIUM | 80651 | 862754 | 116007 | 38406 | 315783 | 29147 |
| MANGANESE | 173 | 310 | 1835 | 158 | 52 | 30 |
| MOLYBDENUM | 14 | 73 | 16 | 12 | 20 | 2 |
| NICKEL | 73 | 146 | 237 | 145 | 54 | 12 |
| PHOSPHORUS | 141 | 731 | 156 | 93 | 203 | 20 |
| POTASSIUM | 3051 | 33194 | 14338 | 34780 | 10285 | 2111 |
| SELENIUM | 141 | 731 | 156 | 67 | 203 | 20 |
| SILICON | 702 | 2574 | 286 | 521 | 576 | 179 |
| SILVER | <14 | <73 | <16 | <7 | <20 | <2 |
| STRONTIUM | 906 | 643 | 740 | 1356 | 568 | 95 |
| SODIUM | 132438 | 127512 | 18443 | 51163 | 29630 | 2603 |
| THALLIUM | <28 | <146 | <31 | <13 | <41 | <4 |
| VANADIUM | <14 | <73 | <16 | <7 | <20 | <2 |
| ZINC | 82 | 11187 | 526 | 422 | 375 | 32 |

EXAMPLE 2

A group of the surface electrodes have been used experimentally in mineral exploration on the Pebble Copper Porphyry prospect in Alaska, U.S.A. The surface area is covered by glacially derived gravels. Soil geochemistry did not give results that were diagnostic of buried mineralization. In comparison, the surface geo-electrochemistry results from the surface electrode gave excellent indications of a buried copper deposit.

There the collectrode was useful in extracting copper, molybdenum, zinc, lead and various other ions from the rock forming minerals such as sodium and potassium from over 200 feet of glacial cover. This was in an area where normal soil geochemistry did not function.

The Pebble Copper Project area was surveyed by two lines using the collectrodes and geo-electrochemical sampling procedures according to the invention. The survey was selected as a test because it had been mapped, it had prior geophysics run on it and it had been drilled. This area is also covered by glacial debris and normal soil samples do not reflect the presence of copper at depth.

The purpose of the test was to determine if anomalous values of copper would be indicated using the Geo-electrochemical sampling procedures of the invention in areas of known mineralization covered by up to 250 feet of glacially derived material, where no appreciable soil sample anomaly was present when normal geochemical soil sampling procedures were employed. This was considered to be an ideal test since normal soil sampling procedures gave little indication of the amount of copper at depth. The reason for this is that the soil was derived from transported material (by glacier) and the soil does not reflect the copper deposit covered by some 250 feet of this transported material. The area had also been surveyed with induced polarization and resistivity. This allowed the correlation of the Geo-electrochemical results with that of the drilling, soil sampling, geology, and induced polarization surveys. The test Line 570+00 was also over a mineralized portion of the project. Line 388+00 was over lower values of copper.

The Geo-electrochemical test was run using normal field operating procedures. The collectrodes were placed along Line 570+00 N at 200 foot intervals over a length of some 2000 feet. The tests were run over a three day period. The cation exchange resins in the collectrodes were then collected, ashed, weighed, and analyzed using ICP. The results from the ICP were reported in ppm (parts per million) and percent. The value of the analyzed material was multiplied by the weight of the ash giving values in µg (micrograms). This value was then divided by the product of current multiplied by time (amp hours or ah), to give µg/ah. This value is useful when comparing values from one area to the next.

Another perhaps more meaningful method is to divide that value by the gram molecular weights of each element involved resulting in the µgmw/ah. This is a more important term when doing Geo-electrochemical testing. This allows the comparison of values from area to area, and different elements, one to each other. This term is also referred to by Cominco (an international mining company) as a Geo-electrochemical Sampling Unit (GSU). This is reported in µgmw/ah, (microgram molecular weights)/(amp hours).

Since, however, most other experimenters report data in ppm, or µg/ah, we have reported using those systems, so that a meaningful comparison can be made with reported data from other systems.

The data from the soil sample for copper are shown in Table 2. The geostatistical analysis of all of the copper in the soils indicates that values of over 125 ppm Cu can be considered anomalous >80 percentile. Thus the line is lower than that threshold level. The values are not anomalous, and are not representative of the copper in the rocks because of the fact that the soil is transported from a remote site by glacial activity.

Table 2 also contains the results from the Geo-electrochemical sampling program for the same locations as the soil samples. The values are shown as ppm for copper for the Geo-electrochemical sampling program and are extremely high.

TABLE 2

| Station | Ashed Resin Geo-electrochemistry | | Soil |
|---|---|---|---|
| | ppm Cu | (µg/ah) Cu | ppm Cu |
| 57400 | 4900 | 42380 | 45 |
| 59900 | 4000 | 95420 | 35 |
| 60158 | 19900 | 96290 | 23 |
| 60300 | 7300 | 654670 | 30 |
| 60500 | 7600 | 265140 | 25 |
| 60700 | 16000 | 244140 | 19 |
| 60900 | 36800 | 258320 | 19 |

The above is only part of the line sampled. The average for the entire line was 229346 µg/ah with the highest value at 654670 µg/ah. The U.S. Geological Surveys reports that results of 1200 µg/ah are extremely anomalous, being the highest that they had collected. Thus these values of 22934 µg/ah definitely are anomalous, indicating both a high level of Cu ions in the ground water, and an extremely efficient ion collecting electrode. The line was not extended far enough east or west to obtain background readings. Other testing and logic dictates that values should gradually decrease away from the copper bearing zone reaching background levels of 4 to 5 ppm or 40 to 50 µg/ah. However, hydrodynamic dispersion from a large source such as a porphyry will create a large dispersion halo.

The copper values can be compared to other rock forming minerals such as calcium, iron, magnesium and potassium, as well as for those lesser metals such as lead, zinc, manganese, if the values are reported in µgmw/ah.

Table 3 gives the result for the value of other selected elements on line 570+00 and 388+00 reported in µg/ah, and the expected relationship as determined from normal porphyry zonal patterns.

TABLE 3

| Element | Line 570+00 µg/ah | Line 388+00 µg/ah | Expected Relationship |
|---|---|---|---|
| Cu | 229364 | 144941 | 570+00 > 388+00 |
| Zn | 24547 | 38934 | 570+00 < 388+00 |
| K | 624515 | 154097 | 570+00 > 388+00 |
| Pb | 7517 | 4310 | 570+00 < 388+00 |
| Si | 177619 | 103420 | 570+00 > 388+00 |
| Fe | 70912 | 60771 | 570+00 > 388+00 |
| Mo | 103.6 | 90.2 | 570+00 > 388+00 |

The copper values for line 388+00 are less than 570+00 N by a factor of 2. This is the correct relationship since there was less copper there. There seems to be hydrodynamic dispersion of copper in that direction.

Table 3 is a listing of other selected elements that were sampled. The results reported are the average for that line. The interesting feature in these data is that the elements reflect the basic composition of the host rock and alteration of the host rock. Porphyry copper deposits have a large potassium enriched core near the mineralization. The average value for potassium for line 570+00 N is 624515 µg/ah and line 388+00 N is 154097 µg/ah. This indicates that the ions sampled for line 570+00 N were derived from rock which contained much more potassium than line 388+00 N. Line 570+00 N is generally inside the main mineralization and line 388+00 N is outside the main mineralization. The potassium values from the geo-electrochemistry sampling indicate the correct relationship of the potassium values of the rocks from which the ions were derived. The other elements listed indicated the correct zonal alteration patterns that one would see by doing whole rock geochemistry, with the exception of lead (Pb). Thus the ions sampled using the collectrode and the geo-electro-chemical sampling procedures of the invention seem to reflect the make-up of the whole rock. Thus it is possible that the geo-electrochemistry of the invention has been sensitive enough to indicate whole rock geochemistry.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A method of sampling and analyzing ground water for underlying metallic ions contained in the ground water which comprises:

(a) applying a negative voltage in the range of 200 to 2,000 volts DC to a cathode immersed in generally ion-free water proximate to the ground water thereby attracting metallic cations contained in the ground water to the cathode;

(b) exchanging the attracted metallic cations for hydrogen ions contained in a hydrogen ion charged ion exchange resin also immersed in mid generally ion-free water to thereby deposit the metallic cations on the ion exchange resin and release the hydrogen ions from the exchange resin to the cathode; and (c) analyzing the concentration of metallic cations deposited on the ion exchange resin.

2. A method as claimed in claim 1 which comprises ashing the ion exchange resin which holds the deposited metallic cations to form an ashed product and analyzing the metallic cations in the ashed product.

3. A method as claimed in claim 2 which comprises analyzing the ashed ion exchange resin product by inductively coupled plasma mass spectrometry.

4. A method as claimed in claim 1 wherein the generally ion free water is distilled water or purified water.

5. A method of focusing a collection electrode which is used to attract cations in ground water which comprises:

(a) deploying a central hollow collection electrode containing ion exchange resin and generally ion-free water on or near the surface of ground in which ground water is found, and applying a negative voltage in the range 200 to 2,000 volts DC to the electrode proximate to the ground water to attract cations to the collection electrode; and (b) deploying at least one peripheral focusing electrode on or near the surface of the ground adjacent to but spaced from the central collection electrode and applying approximately the same voltage as that applied to the central collection electrode to thereby focus the cations attracted to the central collection electrode.

6. A method as claimed in claim 5 which comprises spatially deploying at least four peripheral collectrodes around the periphery of the central collection electrode so that the central collection electrode tends to attract metallic cations in the ground water from the side and below the central collection electrode.

7. A method of focusing a downhole collection electrode to sample ions in ground water which comprises:

(a) dividing the collection electrode into a first upper compartment, a second middle compartment and a third bottom compartment, said compartments being separate from each other and each containing ion exchange resin;

(b) deploying the collection electrode in a drill hole below ground level;

(c) applying a high potential to the collection electrode, whereby the first compartment of the collection electrode tends to collect ions from above and beside the upper region of the collection electrode to the ion exchange resin contained in the first compartment, whereby the second compartment of the collection electrode tends to attract ions located laterally of the collection electrode to the ion exchange resin contained in the second middle compartment; and the third bottom compartment of the collection electrode tends to attract ions located beside and below the lower region of the collection electrode to the ion exchange resin contained in the third bottom compartment of the collection electrode.

8. A method as claimed in claim 7 which comprises applying a negative voltage to the collection electrode so that metallic ions in the ground water are attracted to the first, second and third compartments of the collection electrode.

9. A method as claimed in claim 7 wherein the downhole collection electrode contains generally ion-free water.

10. A method of determining metal ion contamination in ground waters in the region of an industrial installation which comprises deploying an array of collection electrodes containing ion exchange resins and generally ion free water in the region of the industrial installation, negatively charging the collection electrodes on a periodic basis with a voltage in the range 200 to 2,000 volts DC to attract metal ions in the ground water surrounding the industrial installation to the respective collection electrodes and ion exchange resins, and sampling the ion exchange resins on a periodic basis to determine the extent of metal ion contamination in the ground water.

* * * * *